(12) United States Patent
Faltys

(10) Patent No.: US 7,107,101 B1
(45) Date of Patent: Sep. 12, 2006

(54) BIONIC EAR PROGRAMMING SYSTEM

(75) Inventor: Michael A. Faltys, Northridge, CA (US)

(73) Assignee: Advanced Bionics Corporation, Valencia, CA (US)

( * ) Notice: Subject to any disclaimer, the term of this patent is extended or adjusted under 35 U.S.C. 154(b) by 514 days.

(21) Appl. No.: 10/218,616

(22) Filed: Aug. 13, 2002

Related U.S. Application Data

(60) Provisional application No. 60/313,225, filed on Aug. 17, 2001.

(51) Int. Cl.
*A61N 1/18* (2006.01)
(52) U.S. Cl. .......................... 607/55; 607/57
(58) Field of Classification Search ............. 607/55–57
See application file for complete search history.

(56) References Cited

U.S. PATENT DOCUMENTS

| | | | |
|---|---|---|---|
| 3,751,605 A | | 8/1973 | Michelson |
| 4,400,590 A | | 8/1983 | Michelson |
| 4,612,934 A | * | 9/1986 | Borkan ......................... 607/62 |
| 5,003,975 A | * | 4/1991 | Hafelfinger et al. .......... 607/28 |
| 5,609,616 A | * | 3/1997 | Schulman et al. ............ 607/56 |
| 5,626,629 A | | 5/1997 | Faltys et al. |
| 6,067,474 A | | 5/2000 | Schulman et al. |
| 6,129,753 A | | 10/2000 | Kuzma |
| 6,157,861 A | | 12/2000 | Faltys et al. |
| 6,205,360 B1 | * | 3/2001 | Carter et al. ................... 607/57 |
| 6,219,580 B1 | | 4/2001 | Faltys et al. |
| 6,249,704 B1 | | 6/2001 | Maltan et al. |
| 6,289,247 B1 | | 9/2001 | Faltys et al. |
| 6,751,505 B1 | * | 6/2004 | Van Den Honert et al. ... 607/57 |
| 6,778,858 B1 | * | 8/2004 | Peeters .......................... 607/57 |
| 6,915,166 B1 | * | 7/2005 | Stecker et al. ................ 607/55 |

FOREIGN PATENT DOCUMENTS

| | | | |
|---|---|---|---|
| WO | WO01/15773 | * | 3/2001 |
| WO | WO 01/19304(A1) | | 3/2001 |

OTHER PUBLICATIONS

Using impedance telemetry to diagnose cochlear electrode history, location, and fuctionality, Schulman, The Annals of Otology, Rhinology & Laryngology Suppl. Sep. 1995, vol. 166, pp. 85-87.*
Comparative speech recognition results in eight subjects using two different coding strategies with the Nucleus 22 channel cochlear implant, von Wallenberg et al., Br J Audiol., Dec. 1991, Abstract.*

* cited by examiner

*Primary Examiner*—George Manuel
*Assistant Examiner*—Nicole R. Kramer
(74) *Attorney, Agent, or Firm*—Bryant R. Gold; Victoria A. Poissant

(57) ABSTRACT

A method of programming a bionic ear cochlear implant provides access to the full functionality of the implant, while still providing a simple-to-administer, more reliable, and faster fitting experience for the patient and clinician. The method includes (a) conducting a pre-evaluation stage focused on sorting and identifying bad electrode contacts, reducing fitting time and improving patient performance; (b) conducting a programming stage wherein T and M levels are adjusted based on information derived during the pre-evaluation stage; and (c) conducting a post-evaluation stage wherein wired speech understanding tests are automatically run in order to provide an objective programming choice. The pre-evaluation stage automatically runs a set of objective tests, and then, based on the result of such tests, generates a template for the clinician to use during the programming stage. The objective tests, inter alia, identify and remove bad electrode contacts from the template. The post-evaluation stage quickly runs some unattended wired speech understanding tests that allow objective rather than subjective programming choices to be made.

14 Claims, 2 Drawing Sheets

BIONIC EAR PROGRAMMING SYSTEM

The present application claims the benefit of U.S. Provisional Application Ser. No. 60/313,225, filed Aug. 17, 2001, which application is incorporated herein by reference.

BACKGROUND OF THE INVENTION

The present invention relates to cochlear implants, and more particularly to a bionic ear programming system that may be used with the more sophisticated and complex cochlear implants that are now available.

Electrical stimulation of predetermined locations within the cochlea of the human ear through an intra-cochlear electrode array is described, e.g., in U.S. Pat. No. 4,400,590. The electrode array shown in the '590 patent comprises a plurality of exposed electrode pairs spaced along and imbedded in a resilient curved base for implantation in accordance with a method of surgical implantation, e.g., as described in U.S. Pat. No. 3,751,615. The system described in the '590 patent receives audio signals, i.e., sound waves, at a signal processor (or speech processor) located outside the body of a hearing impaired patient. The speech processor converts the received audio signals into modulated RF data signals that are transmitted by a cable connection through the patient's skin to an implanted multi-channel intracochlear electrode array. The modulated RF signals are demodulated into analog signals and are applied to selected ones of the plurality of exposed electrode pairs in the intra-cochlear electrode so as to electrically stimulate predetermined locations of the auditory nerve within the cochlea.

A new, more sophisticated, class of cochlear implant, referred to as a bionic ear, is now available to provide patients with enhanced hearing performance. For example, Advanced Bionics Corporation, of Sylmar Calif., currently offers a cochlear implant which it refers to as the CII Bionic Ear™ cochlear implant. Many features associated with the CII Bionic Ear implant are described in U.S. Pat. No. 6,219,580, incorporated herein by reference. Advantageously, with the CII Bionic Ear™ cochlear implant, more than twice as much sound can be captured, and 10 times more processing power is available to process such sound. Further, the CII Bionic Ear implant contains internal memory banks that enable it to send very detailed, high resolution sound signals to the auditory nerve. Such signals are delivered to the auditory nerve using a special electrode adapted to be inserted into the cochlea. A representative electrode usable with the CII Bionic ear is described in U.S. Pat. No. 6,129,753, also incorporated herein by reference.

Other improved features of cochlear implant systems are taught, e.g., in U.S. Pat. Nos. 5,626,629; 6,067,474; 6,157,861; 6,219,580; 6,249,704; and 6,289,247, each of which patents is incorporated herein by reference.

Advantageously, the implantable cochlear stimulators described in the '629, '474, '861, '580 and '704 patents are able to selectively control the pulse width of stimulating pulses that are applied through the electrode array to the cochlea, and the frequency at which the stimulating pulses are applied.

As the art of cochlear stimulation has advanced, the implanted portion of the cochlear stimulation system, and the externally wearable processor (or speech processor), if used (much of the circuitry previously employed in the externally wearable processor has been moved to the implanted portion, thereby reducing the amount of information that must be transmitted from the external wearable processor to the implanted portion), have become increasingly complicated and sophisticated. The amount of control and discretion exercisable by an audiologist in selecting the modes and methods of operation of the cochlear stimulation system have increased dramatically and it is no longer possible to fully control and customize the operation of the cochlear stimulation system through the use of, for example, switches located on the speech processor. As a result, it has become necessary to utilize an implantable cochlear stimulator fitting system to establish the operating modes and methods of the cochlear stimulation system and then to download such programming into the speech processor. One such fitting system is described in the '629 patent. An improved fitting system is described in the '247 patent. The present invention is directed to a still further improved fitting system that may be used with a bionic ear cochlear implant.

The '247 patent further highlights representative stimulation strategies that may be employed by a multichannel stimulation system. Such strategies represent the manner or technique in which the stimulation current is applied to the electrodes of an electrode array used with the stimulation system. Such stimulation strategies, all of which apply current pulses to selected electrodes, may be broadly classified as: (1) sequential or non-simultaneous (where only one electrode receives a current pulse at the same time); (2) simultaneous (where substantially all of the electrodes receive current stimuli at the same time, thereby approximating an analog signal); or (3) partially simultaneous pulsitile stimulation (where only a select grouping of the electrodes receive stimuli at the same time in accordance with a predefined pattern).

Typically, when the fitting systems described in the '629 or '247 patents are employed for multichannel stimulation systems, or when equivalent or similar fitting systems are employed, it is necessary to use directly measured threshold values and/or thresholds derived from the measurement of phsycophysically-determined psuedo-comfort levels. That is, for each channel of the multichannel system, a minimum threshold level is measured, typically referred to as a "T" level, which represents the minium stimulation current which when applied to a given electrode associated with the channel produces a sensed perception of sound at least 50% of the time. In a similar manner, an "M" level is determined for each channel, which represents a stimulation current which when applied to the given electrode produces a sensed perception of sound that is moderately loud, or comfortably loud, but not so loud that the perceived sound is uncomfortable. These "T" and "M" levels are then used by the fitting software in order to properly map sensed sound to stimulation current levels that can be perceived by the patient as sound.

Disadvantageously, determining the "T" and/or "M" levels (or other required thresholds) associated with each channel of a multichannel stimulation system is an extremely laborious and time-intensive task. Such determinations require significant time commitments on the part of the clinician, as well as the patient. Moreover, once determined one channel at a time, such levels may not be representative of actual threshold levels that are present during real speech.

SUMMARY OF THE INVENTION

The present invention provides a Bionic Ear Programming System (BEPS) that provides access to the full functionality of a bionic ear implant, such as the CII Bionic Ear™ implant made by Advanced Bionics Corporation.

Equally important, the BEPS of the present invention supports a much more complex device than previous programming systems from the point of view of a clinician fitting the patient.

The added complexity provided in a bionic ear implant, such as the CII Bionic Ear™ implant, includes higher numbers of channels, arbitrary simultaneous grouping, intraphase gaps, binaural capabilities, and the like. Fortunately, the BEPS deals with all of this added complexity in a way that makes the new, more complex bionic ear implant, seem easier to use and fit. That is, while the BEPS adds tools to take advantage of the increased functionality of the implant, such tools are fashioned to help the clinician fit a patient faster and more accurately than has heretofore been possible. For example, rather than expanding the process of setting T's and M's into a multi-window workflow, all of this functionality has been included in a single window. Additionally, such single functionality within one single window is segmented into an easy-to-use 3-part workflow, as explained hereinafter.

In accordance with one aspect of the invention, the BEPS automatically finds and removes broken electrodes, thereby preventing stimulation on such electrodes, and thereby further eliminating the need for the clinician to measure impedances and manually remove such broken electrodes. The result is a much more safer programming system.

It is a feature of the present invention to provide a programming system that automatically sorts out bad electrodes, reduces fitting times and improves patient performance.

It is yet another feature of the invention to provide a programming system that automatically generates customized programming templates that a clinician may use to quickly fit a given patient.

It is an additional feature of the invention to provide a programming system that allows clinicians to quickly run (unattended) wired speech understanding tests that provide objective rather than subjective programming choices.

BRIEF DESCRIPTION OF THE DRAWINGS

The above and other aspects, features and advantages of the present invention will be more apparent from the following more particular description thereof, presented in conjunction with the following drawings wherein.

Figure 1A:
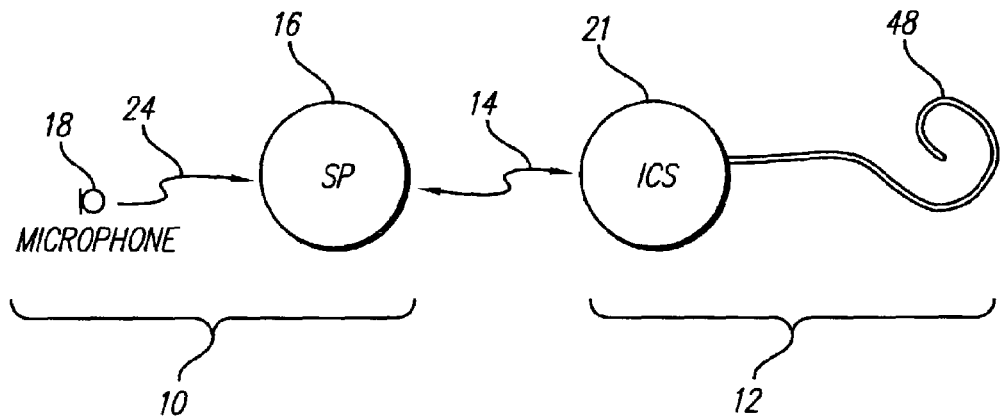
FIG. 1A shows a typical bionic ear implant system.

Appendix A, incorporated herein by reference, provides an overview of various features associated with the BEPS of the present invention.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention.

Turning first to FIG. 1A, a bionic ear cochlear stimulation system is shown that includes a speech processor portion 10 and a cochlear stimulation portion 12. The speech processor portion 10 includes a speech processor (SP) 16 and a microphone 18. The microphone 18 may be connected directly to the SP 16, or may be coupled to the SP 16 through an appropriate communication link 24. The cochlear stimulation portion 12 includes an implantable cochlear stimulator (ICS) 21, and an electrode array 48. The electrode array 48 is adapted to be inserted within the cochlea of a patient. The array 48 includes a multiplicity of electrodes, e.g., sixteen electrodes, spaced along its length that are selectively connected to the ICS 21. The electrode array 48 may be substantially as shown and described in U.S. Pat. No. 4,819,647 or 6,129,753, incorporated herein by reference. Electronic circuitry within the ICS 21 allows a specified stimulation current to be applied to selected pairs or groups of the individual electrodes included within the electrode array 48 in accordance with a specified stimulation pattern, defined by the SP 16.

The ICS 21 and the SP 16 are shown in FIG. 1A as being linked together electronically through a suitable data or communications link 14. In some cochlear implant systems, e.g., prior art systems, the SP 16 and microphone 18 comprise the external portion of the cochlear implant system; and the ICS 21 and electrode array 48 comprise the implantable portion of the system. Thus, the data link 14 is a transcutaneous data link that allows power and control signals to be sent from the SP16 to the ICS 21. In some embodiments, data and status signals may also be sent from the ICS 21 to the SP 16.

In a typical bionic ear implant system, as shown more particularly below in FIG. 1B, at least certain portions of the SP 16 are included within the implantable portion of the overall cochlear implant system, while other portions of the SP 16 remain in the external portion of the system. In general, at least the microphone 18 and associated analog front end (AFE) circuitry will be part of the external portion of the system; and at least the ICS 21 and electrode array 48 are part of the implantable portion of the invention. As used herein, "external" means not implanted under the skin or residing within the inner ear. However, "external" may mean within the outer ear, including in the ear canal, and may also include within the middle ear.

Typically, where a transcutaneous data link must be established between the external portion and implantable portions of the system, such link is realized by an internal antenna coil within the implantable portion, and an external antenna coil within the external portion. In use, the external antenna coil is positioned so as to be aligned over the location where the internal antenna coil is implanted, allowing such coils to be inductively coupled to each other, thereby allowing data (e.g., the magnitude and polarity of a sensed acoustic signals) and power to be transmitted from the external portion to the implantable portion. Note, in other embodiments of the invention, both the SP 16 and the ICS 21 may be implanted within the patient, either in the same housing or in separate housings. If in the same housing, the link 14 may be realized with a direct wire connection within such housing. If in separate housings, as taught, e.g., in U.S. Pat. No. 6,067,474, incorporated herein by reference, the link 14 may be an inductive link using a coil or a wire loop coupled to the respective parts.

The microphone 18 senses acoustic signals and converts such sensed signals to corresponding electrical signals, and may thus be considered as an acoustic transducer. The electrical signals are sent to the SP 16 over a suitable electrical or other link 24. The SP 16 processes these converted acoustic signals in accordance with a selected speech processing strategy in order to generate appropriate control signals for controlling the ICS 21. Such control signals specify or define the polarity, magnitude, location (which electrode pair receives the stimulation current), and timing (when the stimulation current is applied to the electrode pair) of the stimulation current that is generated by the ICS. Such control signals thus combine to produce a desired spatiotemporal pattern of electrical stimuli in accordance with the desired speech processing strategy. Unlike prior art cochlear implant systems, the bionic ear implant system advantageously confines such control signals to circuitry within the implantable portion of the system, thereby avoiding the need to continually send or transmit such control signals across a transcutaneous link.

The speech processing strategy is used, inter alia, to condition the magnitude and polarity of the stimulation current applied to the implanted electrodes of the electrode array 48. Such speech processing strategy involves defining a pattern of stimulation waveforms that are to be applied to the electrodes as controlled electrical currents. If multiple electrode pairs exist, as is the case with a multichannel cochlear implant system, then the types of stimulation patterns applied to the multiple channels may be conveniently categorized as: (1) simultaneous stimulation patterns, or (2) non-simultaneous stimulation patterns. Simultaneous stimulation patterns may be "fully" simultaneous or partially simultaneous. A fully simultaneous stimulation pattern is one wherein stimulation currents, either analog or pulsitile, are applied to the electrodes of all of the available channels at the same time. A partially simultaneous stimulation pattern is one wherein stimulation currents, either analog or pulsitile, are applied to the electrodes of two or more channels, but not necessarily all of the channels, at the same time. Examples of each type are given in the U.S. Pat. No. 6,289,247, previously incorporated herein by reference.

Analog waveforms used in analog stimulation patterns are typically reconstructed by the generation of continuous short monophasic pulses (samples). The sampling rate is selected to be fast enough to allow for proper reconstruction of the temporal details of the signal. An example of such a sampled analog stimulation pattern is a simultaneous analog sampler (SAS) strategy.

Current pulses applied in pulsitile stimulation patterns are generally biphasic pulses, but may also be multiphasic pulses, applied to the electrodes of each channel. The biphasic/multiphasic pulse has a magnitude (e.g., amplitude and/or duration) that varies as a function of the sensed acoustic signal. (A "biphasic" pulse is generally considered as two pulses: a first pulse of one polarity having a specified magnitude, followed immediately, or after a very short delay, by a second pulse of the opposite polarity having the same total charge, which charge is the product of stimulus current times duration of each pulse or phase.) For multichannel cochlear stimulators of the type used with the present invention, it is common to sample the acoustic signal at a rapid rate, and apply a biphasic stimulation pulse in sequence (i.e., non-simultaneously) to each of the pairs of electrodes of each channel in accordance with a specified pattern and cycle time, with the magnitude of the stimulation current being a function of information contained within the sensed acoustic signal at a given (e.g., the most recent) sample time. An example of such sequential, non-simultaneous stimulation pattern is a continuous interleaved sampler (CIS) strategy.

It is important to recognize that in between the two extremes of fully simultaneous stimulation patterns (wherein analog stimulation currents are continuously applied to all channels, e.g., using the SAS strategy) and non-simultaneous pulsitile patterns (wherein biphasic pules are applied in a specified sequence to all channels without time overlap, e.g., using the CIS strategy), there are a great number of other stimulation patterns that may be formulated. Such other simulation patterns may prove more efficacious for a given patient than either of the SAS or CIS strategies. Thus, an important part of the fitting process is identifying which of several speech processing strategies is most beneficial for a given patient. A bionic ear implant assumes that an appropriate speech processing strategy has been identified, or can be easily identified.

Returning to FIG. 1B, a partial block diagram of a representative bionic ear cochlear implant is shown. More particularly, FIG. 1B shows a partial functional block diagram of the SP 16 and the ICS 21 of an exemplary bionic ear cochlear implant system. That which is shown in FIG. 1B depicts the functions that are carried out by the SP 16 and the ICS 21. The actual electronic circuitry that is used to carry out these functions is not critical to the present invention. It should also be pointed out that the particular functions shown in FIG. 1B are representative of just one type of signal processing strategy that may be employed (which divides the incoming signal into frequency bands, and independently processes each band). Other signal processing strategies could just as easily be used to process the incoming acoustical signal, and the present invention could still be used to provide added flexibility in specifying the stimulation patterns and waveforms that are selected and used with such additional signal processing strategies.

Figure 1B:
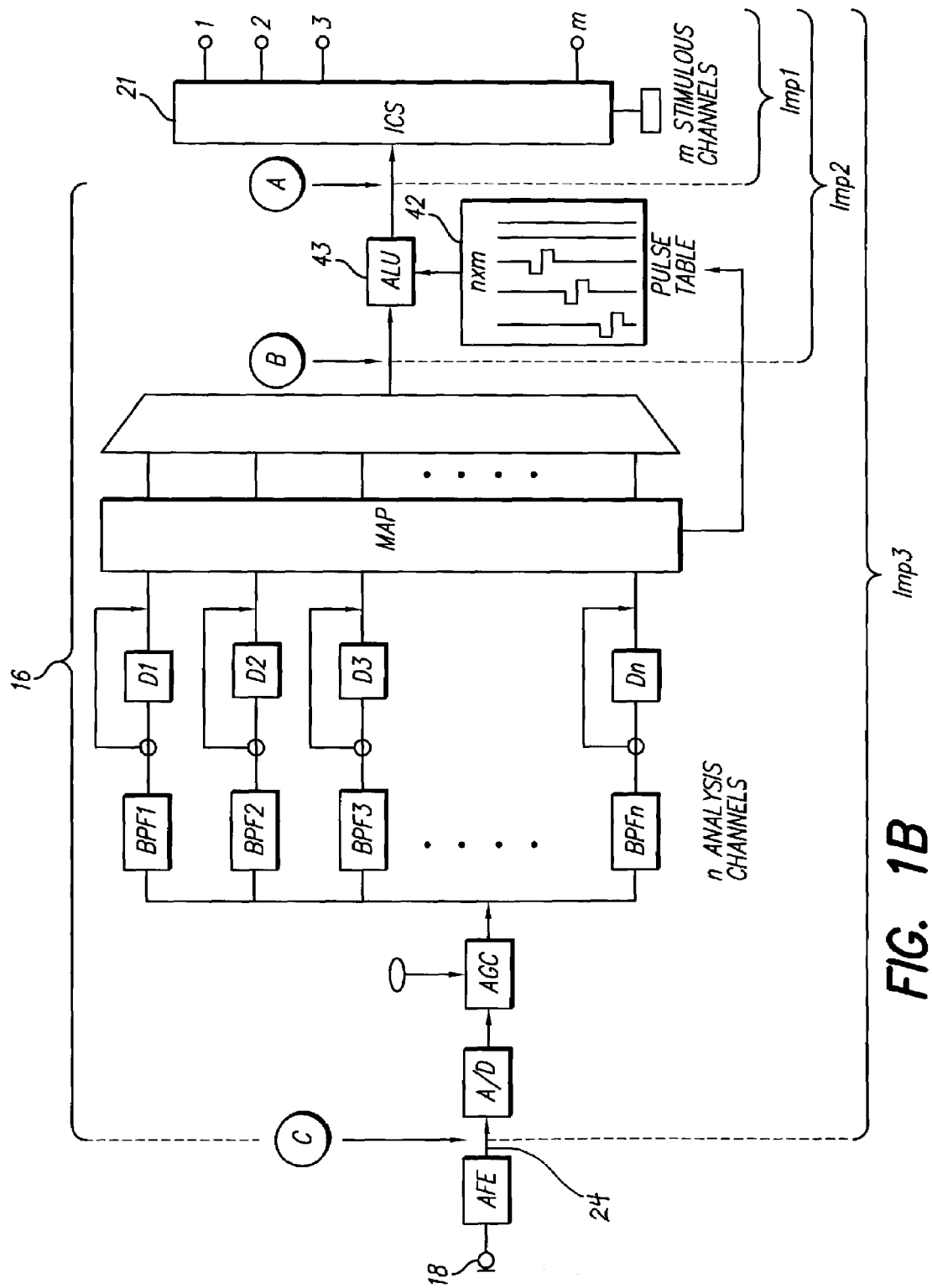
FIG. 1B is a block diagram of a typical bionic ear system.

A complete description of the partial functional block diagram of the bionic ear implant shown in FIG. 1B is found in U.S. Pat. No. 6,219,580, incorporated herein by reference. It is to be emphasized that the bionic ear functionality shown in FIG. 1B is only representative of one type of exemplary bionic ear implant, and is not intended to be limiting. The details associated with a given bionic ear implant are not critical to the present invention.

In the manner described in the '580 patent, the bionic ear implant functionally shown in FIG. 1B provides n analysis channels that may be mapped to one or more stimulus channels. That is, the system of FIG. 1B provides a multiplicity of channels, n, wherein the incoming signal is analyzed. The information contained in these n "analysis channels" is then appropriately processed, compressed and mapped in order to control the actual stimulus patterns that will be applied to the patient by the ICS 21 and its associated electrode array 48. The electrode array 48 includes a multiplicity of electrode contacts, connected through appropriate conductors, to respective current generators, or pulse generators, within the ICS. Through these multiplicity of electrode contacts, a multiplicity of stimulus channels, e.g., m stimulus channels, exist through which individual electrical stimuli may be applied at m different stimulation sites within the patient's cochlea.

While it is common to use a one-to-one mapping scheme between the analysis channels and the stimulus channels, wherein n=m, and the signal analyzed in the first analysis channel is mapped to produce a stimulation current at the first stimulation channel, and so on, it is not necessary to do so. Rather, in some instances, a different mapping scheme may prove beneficial to the patient. For example, assume that n is not equal to m (n, for example, could be at least 20 or as high as 32, while m may be no greater than sixteen, e.g., 8 to 16). The signal resulting from analysis in the first analysis channel may be mapped to the first stimulation channel via a first map link, resulting in a first stimulation site (or first area of neural excitation). Similarly, the signal resulting from analysis in the second analysis channel of the SP may be mapped to the second stimulation channel via a second map link, resulting in a second stimulation site. Also, the signal resulting from analysis in the second analysis channel may be jointly mapped to the first and second stimulation channels via a joint map link. This joint link results in a stimulation site that is somewhere in between the first and second stimulation sites. The "in between site" is sometimes referred to as a virtual stimulation site. Advantageously, this possibility of using different mapping schemes between n SP analysis channels and m ICS stimulation channels to thereby produce a large number of virtual and other stimulation sites provides a great deal of flexibility with respect to positioning the neural excitation areas in a location that proves most beneficial to the patient.

Still with reference to FIG. 1B, it should be noted that the speech processing circuitry 16 generally includes all of the circuitry from point (C) to point (A). In prior art cochlear implant systems, the entire SP circuitry was housed in a speech processor that was part of the external (or non-implanted) portion of the system. That is, in such prior art systems, only the ICS 21, and its associated electrode array, were implanted, as indicated by the bracket labeled "Imp1" (for "Implant-1"). This means that in such prior art systems, the signal passing through the serial data stream at point (A) is also the signal that must pass through the transcutaneous communication link from the external unit to the implanted unit. Because such signal contains all of the defining control data for the selected speech processing strategy, for all m stimulation channels, it therefore has a fairly high data rate associated therewith. As a result of such high data rate, either the system operation must be slowed down, which is generally not desirable, or the bandwidth of the link must be increased, which is also not desirable because the operating power increases.

In contrast to prior art systems, a bionic ear implant advantageously puts at least a portion of the speech processor 16 within the implanted portion of the system. For example, a bionic ear implant places the Pulse Table 42 and arithmetic logic unit (ALU) 43 inside of the implanted portion, as indicated by the bracket labeled "Imp2" in FIG. 1B. Such partitioning of the speech processor 16 offers the advantage of reducing the data rate that must be passed from the external portion of the system to the implanted portion. That is, the data stream that must be passed to the implanted portion Imp2 comprises the signal stream at point (B). This signal is essentially the digitized equivalent of the modulation data associated with each of the n analysis channels, and (depending upon the number of analysis channels and the sampling rate associated with each) may be significantly lower than the data rate associated with the signal that passes through point (A). Hence, improved performance without sacrificing power consumption may be obtained with a bionic ear implant.

It is contemplated that future generations of bionic ear implant systems will incorporate more and more of the speech processor 16 within the implanted portion of the system. For example, a fully implanted speech processor 16 would incorporate all of the SP in the implanted portion, as indicated by the bracket labeled Imp3 in FIG. 1B. Such a fully implanted speech processor would offer the advantage that the data input into the system, i.e., the data stream that passes through point (C), would need only have rate commensurate with the input acoustic signal.

Figure 2:
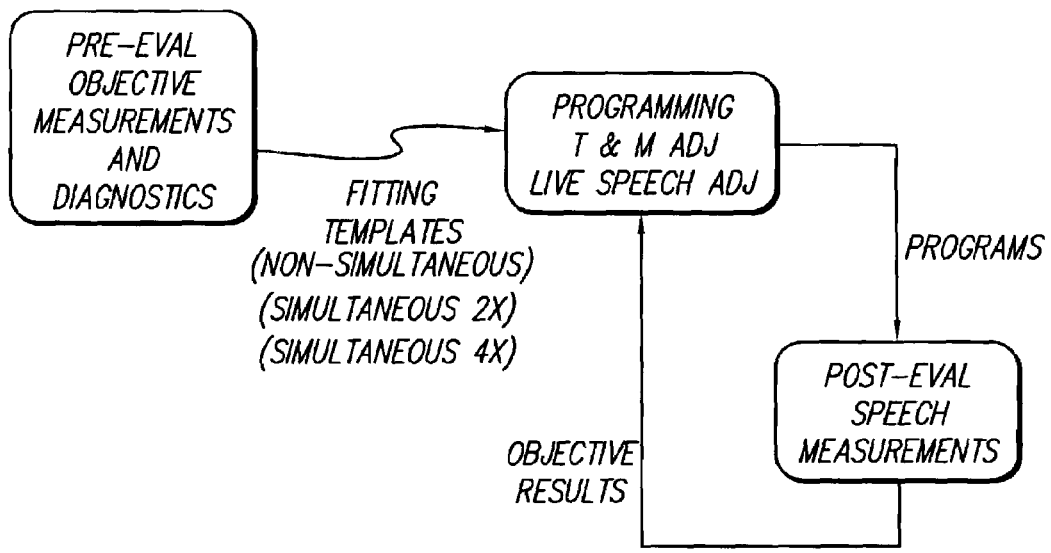
FIG. 2 illustrates the one window, three-part workflow associated with the Bionic Ear Programming System of the present invention.

The BEPS (Bionic Ear Programming System) of the present invention provides access to the full functionality of a bionic ear implant, e.g., the CII Bionic Ear implant. Just as important, however, the BEPS supports a much more complex device than previous systems from the point of view of a clinican fitting a patient using the bionic ear implant. The added complexity of the bionic ear implant includes higher numbers of channels, arbitrary simultaneous grouping, intra-phase gaps, binaural capabilities, and the like. To help deal with this complexity, tools are added to the BEPS that help clinicians fit a patient faster and more accurately. First, rather than expanding the process of setting T's & M's into a multi-window workflow, all of this functionality is placed on one window. Second, the one window where all this functionality is placed is segmented into a 3-part workflow. Such 3-part workflow is illustrated in FIG. 2. See also Appendix A.

Previous, or earlier-generation programming systems, focused entirely on the Programming Stage. Electrode impedances were painstakingly measured, and displayed to the clinician, as a safety feature to prevent stimulation on broken electrodes. The BEPS of the present invention takes a different approach. This is, the BEPS of the present invention takes the position that displaying impedances so the clinician can turn off electrodes is not the correct approach. Such approach disadvantageously emphasized to the clinician and patient that there was something wrong with the patient's system. It is not unusual to have such a condition on a few contacts in an array. Rather than display such a condition to the clinician and the patient, the BEPS of the present invention automatically handles these types of conditions. This approach is also taken when more sensitive tests are deployed. Eliminating the problem electrodes up front is an essential step to obtaining optimal performance.

The first part of the 3-part workflow shown in FIG. 2 is the Pre-Evaluation (Pre-Eval) Stage. During this stage, the BEPS focuses on sorting out bad electrode contacts, reducing fitting times, and improving patient performance. The approach taken by the BEPS is very simple: it runs a set of objective tests, and then generates templates that the clinician uses to start fitting. A template is generated for each type of supported strategy (e.g, CIS, PPS, QPS & N of M). A template excludes suspicious electrodes, sets up necessary simultaneous groups, and estimates relative starting T & M levels. Estimates of the T and M levels are made because it has been found, e.g., during testing, that traditional T & M level measurements have not been accurate. Rather, such measurements have required adjustment by a technique called live-speech adjustment that was pioneered in the original windows-based programming system, known as SCLIN for Windows. (See U.S., e.g., U.S. Pat. No. 5,626,629, previously incorporated herein by reference). NRI-measured T & M levels require the same live-speech adjustment that is already a technique in wide-spread use by clinicians. (NRI-measurements, where NRI stands for Neural Response Imaging, are described, e.g., in U.S. Pat. Nos. 6,157,861 and 6,195,585, incorporated herein by reference, and relate, in general, to monitoring a response evoked by application of a stimulus pulse.) Advantageously, by estimating T and M levels, and including such estimates in the templates, much of the live-speech adjustment can be eliminated or minimized.

The Pre-Eval Stage runs unattended (typically within 5–30 minutes) after an initial setup, and consists of the following steps:

(1) The clinician sets safety levels observing compliance voltage requirements.
(2) An electric field imaging (EFI) test is run to access electrode quality and to eliminate problem electrodes or to notify the clinician if a large percentage of the array is failing a test. The EFI test conditions the array while it is running and runs over and over again until the array measurements stabilize. Such test typically involves, inter alia, determining an RF transfer function at selected operating conditions.
(3) An NRI test is run to check loudness growth on each electrode. Electrodes without loudness growth are eliminated. From this data RELATIVE T & M levels are estimated and reduced for safety purposes.
(4) An AIT (Automatic Electrode Interaction) test is run to estimate the interaction between the electrodes and to assign electrodes into least-interacting groups. This test correlates well to performance. Thus, using this AIT test, a minimum estimated performance score may be provided, setting an objective fitting goal.

As seen in FIG. 2, after the Pre-Eval stage is complete, the Programming stage may commence. Such Programming stage involves conventional programming techniques and methods, e.g., to set and adjust T and M levels, all of which may be completed much faster and more accurately using the templates that are generated during the Pre-Eval stage.

The Post-Eval stage invokes automated speech testing material that allows a clinician to quickly run (unattended) wired speech understanding tests to make objective, rather than subjective, programming choices. A patient's choice of strategy based on preference many times results in reduced performance. This is the way most implants have heretofore been programmed. Advantageously, the objective measures provided in the Post-Eval stage allow the clinician to quantitatively assess performance increases in the overall scores of the bionic ear implant. These tests provide optional "information transfer" indexes, that automatically make adjustments to the patient's program, as needed. Also, at least for the time being, the clinician may use his or her knowledge to manually adjust the patient's cochlear implant program appropriately.

Advantageously, each of the three above-described stages—the pre-evaluation stage, the programming stage, and the post-evaluation stage—may be launched from a single programming window. A representative programming window that may be used for this purpose is described in Appendix A.

While the invention herein disclosed has been described by means of specific embodiments and applications thereof, numerous modifications and variations could be made thereto by those skilled in the art without departing from the scope of the invention set forth in the claims.

APPENDIX A

High Resolution Fitting Software

Figure 13:
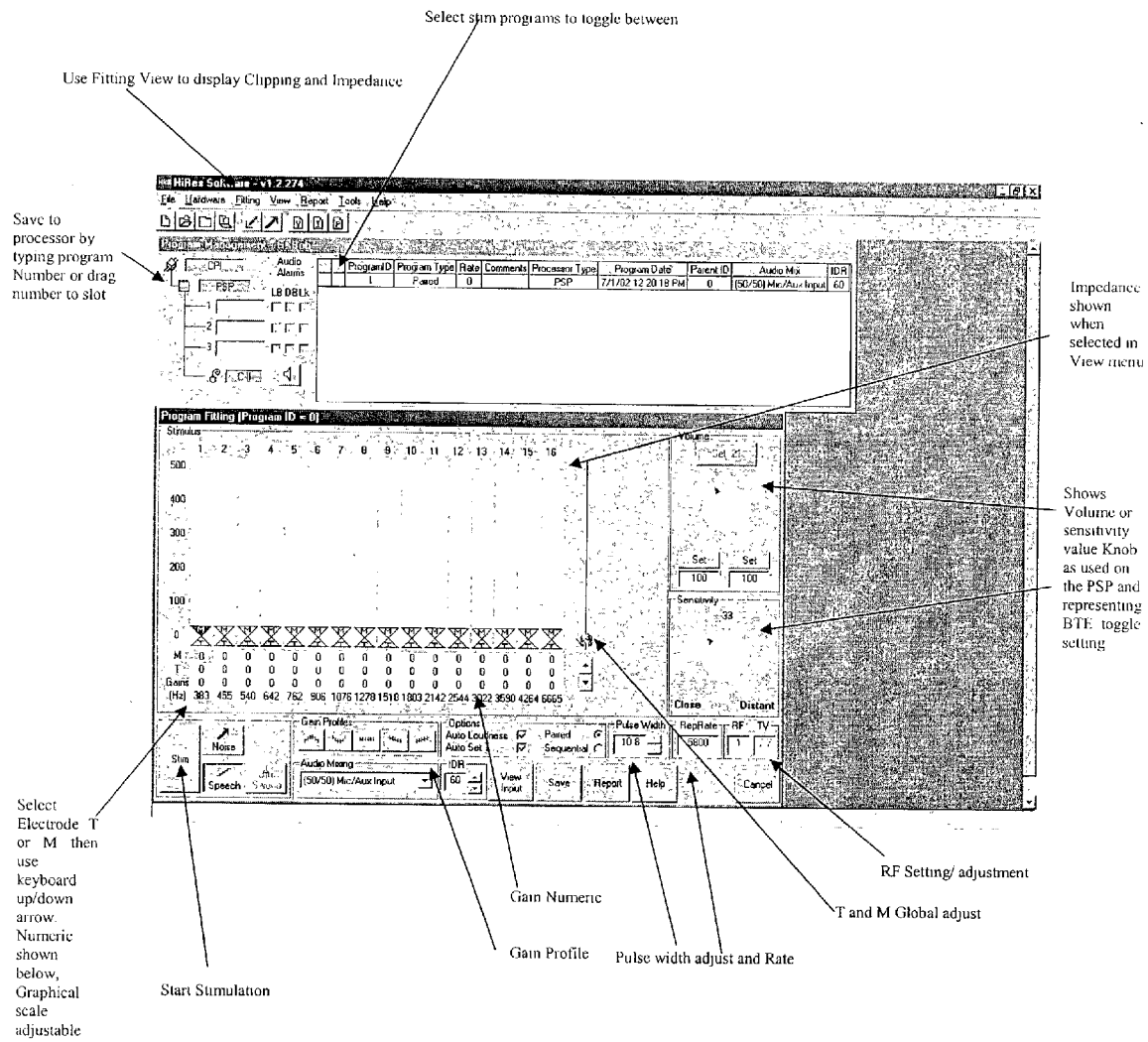

FIG. 13 shows a fitting screen window that is used, in one embodiment of the invention, to aid a clinician, e.g., an audiologist, during a fitting session with a user of a cochlear implant system, e.g., a CII Bionic Ear implant. A fitting session involves setting all of the parameters used by the cochlear implant system so that the patient being fitted can best perceive or "hear" sound.

During a fitting session, a clinician typically connects a user interface module with the bionic ear implant system, and then connects a suitable computer, e.g., a laptop computer, loaded with the appropriate fitting software with the user interface module. The clinician is then able to be guided by the displays and menus provided by the fitting software so that the appropriate stimulation parameters are set within the patient's cochlear implant system. Such a process --of coupling a suitable computer, e.g., a laptop computer, or equivalent, to a cochlear implant system-- may be as described, e.g., in FIG. 2A and 2B and accompanying text of U.S. Patent 6,289,247, previously incorporated herein by reference.

The High Resolution Fitting software is intended to provide a simple, reliable interface for an audiologist to fit a cochlear implant device. The Audiologist is presented with a minimum number of screens to support the major functions required for fitting. The major functional requirements provided by the fitting software include: (1) identify and manage the User, patient, Patient program and fitting History; (2) identify Hardware, Software version, connection status and upload/download of processor program parameters; (3) perform diagnostics on the electrodes and RF Link; (4) perform psychophysics through Audiologist/Patient interaction; and (5) perform program adjustment of parameters for a specific patient.

A series of screens, menu's, dialog boxes and Icon's are used to implement the features of the fitting software. The major screens and windows made available for this purpose are as follows: (a) Windows Desk Top and Program Menu ICON; (b) Anchor screen; (c) Patient selection window; (d) Patient information Window; (e) Diagnostic control dialog box; (f) Program management window; and (g) Fitting Window. Of these, only the Fitting Window screen (FIG. 13) is particularly relevant to the present invention. Moreover, it should be emphasized that neither the Fitting Window, nor the High Resolution fitting software, is needed to practice the invention. That is, the invention is directed to setting T levels to a fixed value, rather than taking the time to individually measure the T-levels for each channel (as has always been done before during a fitting session). Any process or technique, including any of numerous fitting procedures that could be fashioned by a person of skill in the art, that allows for quickly setting the T-levels of each channel to an acceptable level, without having to individually measure them, could be used. That which is described below in conjunction with the Fitting Window (FIG. 13) represents only one way of doing such fitting.

The Fitting screen shown in FIG. 13 is the main working screen for the High Resolution Fitting Software System. This screen provides both Psychophysics and Program fitting on the same screen.

The Fitting screen displays 16 channels of information or 15 in Differential configuration. VU meters are visible for each channel as a graphic representation of output when stimulation is on. The state (enabled or disabled) is also displayed for each channel.

Optional Parameter displays are also available. Impedance readings, for example, are displayed as a numeric presentation when viewed. Additionally, clipping as a graphical symbol showing relative level compared to T and M may be viewed.

In use, channels are enabled or disabled by a right click on the selected channel. The channel order is changeable. Global settings are also possible. For example, T and M values are adjustable as global (all at once) settings.

Automatic Loudness growth is also settable. That is, M and T levels may be increased in charge units based on a default pulse width and current (uA) levels. Charge may be increased by adjusting current as the primary parameter. Pulse width is automatically increased for continued loudness growth when system current limits are reached. The display on the Fitting Screen shows only increased M values and calculated stimulation Rate.

RF Optimization is a further feature accessible through the fitting screen. System voltage limits for delivered RF level are measured for each adjustment of T or M. This Transfer function along with required system power are used to automatically adjust the RF level.

Volume and sensitivity settings are displayed as a knob. Three types of stimulation control are processed through the processor, Speech, Tone and Noise. Each stimulation passes signals through the processor band-pass filters to the stimulation output. When "Speech" control is selected, the system processes live speech from the microphone or external auxiliary input as selected in the Audio mixing screen pull down. When "Tone" is selected, the system measures Psychophysical values. Tone stimulation causes the microphone input to be replaced with a pure tone. A visual cue is presented on the User Interface indicating that Tone stimulation is occurring. Tone selection presents a series of pulses to the selected channel at the selected value (e.g., M or T ). The presentation is made as a series of 200 mS bursts every 750 mS. When Noise is selected, the system operates in Speech mode except the signal is generated internally instead of from the microphone or external auxiliary input. The presentation is made as a series of 200 mS bursts every 750 mS. Stimulation one channel or multiple channels is possible.

Several comparison adjustments may be made, including "Sweep" and "Balance". When "Sweep" is selected, starting at the selected channel, stimulation bursts (Tone or Noise as selected) are presented to each channel sequentially apex to base. The presentation is made as a series of 200 mS bursts every 750 mS. Channel Loudness is equalized by adjusting the M level on the more apical channel. When "Balance" is chosen, stimulation is alternately provided on two channels for loudness or pitch ranking. The keyboard horizontal arrow keys can be used to toggle between selected channels or the channels are alternately stimulated as a series of 200 mS bursts every 750 mS.

Parameter Field descriptions for the Fitting Screen (FIG. 13) are as set forth in Table 1.

TABLE 1

| Item Name | Display | Action | Notes |
|---|---|---|---|
| Electrode Number | Number from 1 to 16 | Display of Electrode number | |
| Impedance value | Measured Impedance for each channel in K ohms | The measured value is displayed at the top of the VU meter for each channel. | Selected in the View Menu Impedance option. |
| Clipping | C in circle shows at the numeric clipping value | The clipping level is the maximum value of output allowed. | |
| Graphical Display of T | Upward Pointing triangle with a "T" inside | Display of T value per channel | Below each channel number is a rectangular area used to display T, M, Clipping and VU meter. T is the |

| Item Name | Display | Action | Notes |
|---|---|---|---|
| | | | Psychophysical level determined for the threshold of hearing |
| Graphical Display of M | Downward Pointing triangle with an "M" inside | Display of M value per channel | M is the Most Comfortable level of hearing determined during Psychophysics |
| Graphical Display of C | Circle with a "C" inside | Display of Clipping value per channel | Clipping is the maximum settable level for a signal |
| VU Meter | Display of input level as graphical bar proportional to input level per channel | Display of output level as graphical bar proportional to output current per channel | Invisible when stimulation is off |
| Numeric value of T | Numeric value | Display | Adjustable by clicking on the Icon, then using the screen up/down arrow, the keyboard up/down arrows or dragging the icon |
| Numeric value of M | Numeric Value | Display | Adjustable by clicking on the Icon, then using the screen up/down arrow, the keyboard up/down arrows or dragging the icon |
| Numeric value of Gain | Numeric Value | Display | Gain setting is made by highlighting the Gain field on a group or individual channel. Gain values may be typed in or gain profiles (Icon) selected and adjusted with arrows. |
| Center Frequency | Numeric value of the channel band-pass filter | Display | |
| Stimulation axis scale | Numeric value placed along y axis Corresponding to charge level | Display | Range is scaled automatically in two ranges as T and M levels are increased. O-1000 ad 0-2000. No Units are shown |
| M, T, Gain, | M, T, Gain, | Label | Label defining the numeric |

| | | | |
|---|---|---|---|
| Frequency Label | HZ | | values. Located on the left side |
| Global adjustment of T and M | Slider bar Icon for T and M | Adjust T and M value | The M value is above the T. Values are increased by dragging the Icon or selecting the Icon and using the arrows. |

Stimulation control fields that may be selected through the Fitting Screen are summarized in Table 2.

TABLE 2

| Item Name | Display | Action | Notes |
|---|---|---|---|
| Start Stimulation Radio Button | Start Icon | Run Working Program | Starts stimulation with mouse click, or "S" keyboard key. Pressing the screen button a second time disables stimulation. Space bar also disables stimulation |
| Speech Radio Button | "Speech" | Select the Speech mode of stimulation | The Speech, Tone, and Noise buttons are mutually exclusive. The Tone button is hidden for the Alpha release. |
| Noise Radio Button * | "Noise" | Select the Noise mode of stimulation | The Speech, Tone, and Noise buttons are mutually exclusive. Selection of Noise to be displayed on the button is made in the Fitting Menu. Noise is the default selection. The Tone button is hidden for the Alpha release |
| Tone Radio Button * | "Tone" | Select the Tone mode of stimulation | The Speech, Tone, and Noise buttons are mutually exclusive. Selection of Tone to be displayed on the button is made in the Fitting Menu. The Tone button is hidden for the Alpha release |

| Item Name | Display | Action | Notes |
|---|---|---|---|
| Sweep Button | Sweep Icon | Select the Sweep mode of stimulation | The Tone or Noise buttons are selected along with the Sweep button |
| Paired | "Paired" check box | Selects Pairing mode of stimulation | Checked when selected. Paired and Sequential are mutually exclusive. When converting from sequential, M and T stimulation levels are reduced by 50%. No change is shown on the display |
| Sequential | "Sequential" check box | Selects Sequential mode of stimulation | Checked when selected. Paired and Sequential are mutually exclusive. When converting from Paired, M and T stimulation levels are increased 2x. No change is shown on the display |

Stimulation actions that may be invoked through the Fitting Screen (FIG. 13) include Noise Stimulation and Tone stimulation. Noise stimulation provides a random white noise signal to each input filter for each electrode. The resulting stimulation provides a stimulation spectrum similar to long term speech spectrum. This stimulation is used to stimulate on 4 adjacent electrodes for even number of active channels and 3 electrodes for odd number of active electrodes to adjust M levels. Switching from groups of 4 electrodes is performed either by manually selecting the first channel or by using the right and left keyboard arrow keys. Sweep mode may be used with Noise stimulation. The stimulation (M) level of all 4 channels are adjusted using the Up arrow (Keyboard and screen) controls.

Tone stimulation provides constant Pulsatile stimulation un-modulated on the channel. Sweep mode may be used with Noise stimulation.

Stimulation Parameters Fields associated with the Fitting Screen (FIG. 13) are as set forth in Table 3.

TABLE 3

| Item Name | Display | Action | Notes |
|---|---|---|---|
| Up/Down Adjust | Arrow radio | Adjust the selected M or T | May also be activated by |

| Item Name | Display | Action | Notes |
|---|---|---|---|
| arrows | buttons vertically placed | levels | keyboard up/down arrow keys. Functions with and without Stimulation on. |
| T and M Gain Profile Button #1 | Mid Frequency Emphasis Icon | Gain profile adjustment | On the numeric gain row, select the channels to apply selection to. Functions with and without Stimulation on. |
| T and M Gain Profile Button #2 | Mid Frequency De-Emphasis Icon | Gain profile adjustment | On the numeric gain row, select the channels to apply selection to. Functions with and without Stimulation on. |
| T and M Gain Profile Button #3 | Flat Emphasis Icon | Gain profile adjustment | On the numeric gain row, select the channels to apply selection to. Functions with and without Stimulation on. |
| T and M Gain Profile Button #4 | Linear Decreasing Emphasis Icon | Gain profile adjustment | On the numeric gain row, select the channels to apply selection to. Functions with and without Stimulation on. |
| T and M Gain Profile Button #5 | Linear Increasing Emphasis Icon | Gain profile adjustment | On the numeric gain row, select the channels to apply selection to. Functions with and without Stimulation on. |
| Interpolate Button | " _ _ _ " | Linear interpolation of T or M value between selected values | Linearly interpolate between T or M settings on 2 selected channels. This function is disabled in the Alpha release software. |
| View Input Button | "View Input" Switches to "Close Window" when the screen shows | Open the input screen (See figure 7A) | The Input screen shows Input VU meters for all channels, IDR indicator bar and Sliders for the gain adjustment. Functions with and without Stimulation on. |
| Sweep Percent | "Sweep" [Value] "%" | Shows the sweep value as a % between T and M setting | This function is disabled in the Alpha Software |
| Repetition Rate | "Repetition Rate" [Rate] | Shows the stimulation repletion rate | The rate is calculated. Functions with Stimulation on. The rate value changes with increases in pulse width. |
| Pulse width adjust | "Pulse Width" | Allows adjustment of the pulse | |

| | With increment and decrement arrows | width when the Auto Loudness growth is de-selected. | |
|---|---|---|---|
| RF Adjust | "RF" with text box | Displays the RF value selected with the RF optimization enabled. When RF optimization is disable from the Tools, Options, Fitting menu, the RF value may be typed in manually | |
| Item Name | Display | Action | Notes |
| Tank Voltage | "TV" with Text box | Displays the Tank voltage read from the processor. Tank voltage is the maximum voltage deliverable to the processor for stimulation | Tank voltaqge may be useful if manual setting of RF is desired. The stimulation current times the electrode impedance should be below the Tank voltage to stay out of compliance. Tank voltage increasing with increasing RF indicated improved power coupling. |
| Save Button | "Save" | Save Active ProgramSave Active Program | An icon shall be provided that will cause the program management to start a program save to Hard disk. |
| Report Button | "Report" | Prints Program Report | See the reports section of this document for description |
| Cancel Button | "Cancel" | Cancel the screen do not save program | Close the fitting screen with patient open. Clicking any program displays the fitting screen for that program |
| Automatic Loudness growth | "Auto Loudness" with a check box | Enables or disables the Automatic Loudness Growth Algorithm | |
| Automatic T scaling | "Auto Set T" with a check box | When checked, the T values are set to 1/10 the value of M per channel. Unchecked T and M are independent | |

The selection pull down field of the Fitting Screen provides the actions shown in Table 4.

TABLE 4

| Item Name | Display | Action | Notes |
|---|---|---|---|
| Audio Mixing | Audio mixing and Pull down list | Select Audio mixing levels | Mixing Ratios shall be set by clicking on a choice from a pull down menu |
| IDR | IDR and IDR pull down list | Select the Input Dynamic Range value | Icon to initiate setting of IDR. Selecting the numeric activates up and down arrows to adjust value. Show button causes pop up of Input VU meter. Hide closes pop-up |
| Pulse width | Shows selected Pulse width | The Pulse width selection overrides the Automatic loudness growth value, by setting the current value of Pulse width. When M value settings reach the ALG compliance value pulse width is incremented per the ALG algorithm. | The value of displayed rate is recalculated when pulse width is changed. Valid pulse width may be found from the equation $10.7us + 0.898 * n$ |

The Volume/Sensitivity Field available on the Fitting Screen (FIG. 13) comprises a field that reflects the position of the Volume and sensitivity controls on the processor. The volume and sensitivity controls appear as knobs on the display. Numerical values showing relative levels are displayed for both Sensitivity and Volume. See Table 5.

TABLE 5

| Item Name | Display | Action | Notes |
|---|---|---|---|
| Volume Set Knob | Knob | Sets Volume of stimulation globally on all electrodes * | Changes numeric display |
| Sensitivity Set Knob | Knob | Selects the gain sensitivity on all channels | The Sensitivity Control modifies the input gain of the signal entering the AGC. The gain can be increased or decreased by +10 or −10 dB. |
| Volume Lower level | Numeric | Displays the lower range of the volume knob | -100 to +100% |

| Item Name | Display | Action | Notes |
|---|---|---|---|
| Volume Upper Level | Numeric | Displays the range of the volume knob | -100 to +100% always greater than Volume Lower Level |
| Volume Lower Level Set Button | "Set" | When pressed sets the lower range of the volume to the selected percentage value | |
| Volume Upper Level Set Button | "Set" | When pressed sets the upper range of the volume to the selected percentage value | |
| Volume 12:00 Set Button | "Set" | When pressed sets the 12:00 value to the selected percentage value | |

The Volume Control allows the user to adjust their M levels while listening. The Volume Control (volpos: -1 (-100%) to 1(100%)) has the effect of shifting the M stimulation levels up or down by a percentage of the electrical dynamic range. The default settings of the upper and lower volume range are +100% and -100% of (M-T). All of the Ms are scaled by the same factor, a percentage of each channel electrical dynamic range as shown in the following equation:

$$M(channel)_{adj} = M(channel) + volpos * [M(channel) - T(channel)]$$

What is claimed is:

1. A method of programming a bionic ear implant comprising;
   conducting a pre-evaluation stage focused on sorting and identifying bad electrode contacts, reducing fitting time and improving patient performance;
   conducting a programming stage wherein T and M levels are adjusted based on information derived during the pre-evaluation stage;
   conducting a post-evaluation stage wherein wired speech understanding tests are automatically run in order to provide an objective programming choice; and
   launching each of the three stages, the pre-evaluation stage, the programming stage, and the post-evaluation stage, from a single programming window;
   wherein said pre-evaluation stage includes generating a template for use during the programming stage that includes estimated T and M levels; and
   wherein generating said template further includes removing from the template bad electrode contacts.

2. The method of claim 1 further including conducting the pre-evaluation stage unattended.

3. The method of claim 2 wherein conducting the pre-evaluation stage comprises:
   performing an initial setup;
   setting safety levels that observe compliance voltage;
   running an Electric Field Imaging (EFI) test to access electrode quality and to eliminate problem electrodes within an electrode array of the bionic ear implant;
   running a Neural Response Imaging (NRI) test to check loudness growth on each electrode used within the electrode array; and
   running an Automatic Electrode Interaction (AIT) test to estimate interaction between electrodes of the electrode array and to assign electrodes into least-interacting groups.

4. The method of claim 3 wherein running the EFI test further includes notifying a clinician if a large percentage of the electrodes within the electrode array are failing the EFI test.

5. The method of claim 3 wherein running the EFI test further comprises running the EFI test over and over again until the electrode array measurements stabilize.

6. The method of claim 3 wherein the step of running an NRI test to test for loudness growth further includes eliminating electrodes without loudness growth.

7. The method of claim 6 further including estimating relative T and M levels using the loudness growth test results.

8. The method of claim 3 further including using the AIT test to provide a minimum estimated performance score, which minimum estimated performance score provides an objective fitting goal.

9. The method of claim 1 wherein conducting the programming stage includes setting and adjusting T and M levels using the template generated during the pre-evaluation stage.

10. The method of claim 1 wherein conducting the post-evaluation stage comprises invoking automated speech testing material adapted to allow unattended wired speech understanding tests to be quickly performed in order to provide objective measures that facilitate quantitative assessment of performance increases of the bionic ear implant.

11. The method of claim 10 further including generating information transfer indexes that allow automatic adjustments to be made to the program of the bionic ear implant.

12. A bionic ear implant programming system comprising:
    means for conducting a pre-evaluation stage focused on sorting and identifying bad electrode contacts, reducing fitting time and improving patient performance;
    means for conducting a programming stage wherein T and M levels are adjusted based on information derived during the pre-evaluation stage;
    means for conducting a post-evaluation stage wherein wired speech understanding tests are automatically run in order to provide an objective programming choice; and
    means for launching each of the three stages, the pre-evaluation stage, the programming stage, and the post-evaluation stage, from a single programming window.

13. The system of claim 12 wherein the means for conducting the pre-evaluation stage further includes means for estimating T and M levels and means for generating a template for use during the programming stage that uses the estimated T and M levels.

14. The system of claim 13 wherein the means for conducting the pre-evaluation stage includes means for removing from the template bad electrode contacts.

* * * * *